(12) United States Patent
Vanmoor

(10) Patent No.: US 6,476,073 B1
(45) Date of Patent: Nov. 5, 2002

(54) METHOD OF TREATING A HANGOVER BY ENHANCING THE EFFECTIVENESS OF THE HUMAN IMMUNE SYSTEM

(76) Inventor: Arthur Vanmoor, 22 SE. 4 St., Boca Raton, FL (US) 33432-6016

( * ) Notice: Subject to any disclaimer, the term of this patent is extended or adjusted under 35 U.S.C. 154(b) by 0 days.

(21) Appl. No.: 09/717,637

(22) Filed: Nov. 21, 2000

(51) Int. Cl.⁷ .............................................. A61K 31/198
(52) U.S. Cl. ....................................... 514/562; 514/563
(58) Field of Search ................................. 514/562, 563

(56) References Cited

U.S. PATENT DOCUMENTS 4,496,548 A * 1/1985 Moldowan et al. ........... 514/27
5,202,354 A * 4/1993 Matsuoka et al. .......... 514/562

FOREIGN PATENT DOCUMENTS

WO         00/59448      * 10/2000

OTHER PUBLICATIONS

Rajakrishnan et al., Amino Acids, 12(3–4), pp. 323–341 (1997) (abstract).*

* cited by examiner

Primary Examiner—Phyllis G. Spivack

(57) ABSTRACT

There is disclosed a method of treating ill effects of alcohol consumption in a person in need of such treatment, which comprises enhancing the effectiveness of the person's immune system by the administration to such person of at least one aliphatic sulfur compound preferably a sulfur-containing amino-acid derivative having the formula (I)

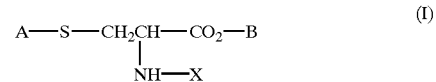

in which A is hydrogen or a carboxymethylene —$CH_2CO_2H$ group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

23 Claims, No Drawings

METHOD OF TREATING A HANGOVER BY ENHANCING THE EFFECTIVENESS OF THE HUMAN IMMUNE SYSTEM

BACKGROUND OF THE INVENTION

1. Field of the Invention

This invention relates to a method of treating a person suffering from the ill effects of ingesting alcohol including dizziness, nausea, blurred vision, and lack of balance, commonly known by the collective term "hangover", with an agent that enhances the effectiveness of the human immune system to mitigate and where possible eliminate the after-effects of alcohol ingestion.

2. Description of Related Art

The human immune system functions to maintain human individuality by fighting off foreign entities. The MERCK MANUAL, 16$^{th}$ edition, published 1992, at pages 279 to 303, which portion is here incorporated by reference, contains a detailed description of the parts of the immune system and of immunodeficiency diseases and hypersensitivity disorders to which it is subject. A table at pages 284–5 titled "Cytokines" lists the major effects of such cytokines or immunoeffective polypeptides as interleukin types, interferon types, alpha- and beta-tumor necrosis factor, three types of colony-stimulating factor, and alpha- and beta-transforming growth factor. A table at page 303 lists disorders with increased susceptibility to unusual infections. Nothing in this publication relates to a hangover condition or remedies therefor.

As is well known, remedies for hangover have been sought for generations by a great variety of methods. However, the search by scientific techniques for better remedies for this as well as other suffering conditions is enormously costly. For economic reasons, moreover, the search tends to be skewed in the direction of finding novel remedies proprietary to their discoverers and owners. Novel remedies, of course, come into being with nothing known about either their safety or their effectiveness, so that both of these essential attributes need to be exhaustively studied before they can be used as intended.

In contrast, the art has tended to neglect the exploration of therapeutic properties of known substances that humans have been safely ingesting for untold generations. Along these lines, the present inventor has been able to bring about in susceptible individuals within a limited and reproducible time the appearance of headache, elevated blood pressure, facial pimples, signs of the so-called common cold, and pains in a joint by administering selected foods, food ingredients, and relatively harmless household chemicals as trigger substances, and to use these as research tools to study the effectiveness of certain nutrient substances in relieving these artificially produced conditions as well as their natural counterparts. As a result, certain water soluble amino carboxylic acid compounds are disclosed in U.S. Pat. No. 5,616,617 as effective against facial pimples; certain water soluble amino carboxylic acid compounds are disclosed in U.S. Pat. No. 5,626,831 as effective against the common cold; certain water soluble amino carboxylic acid compounds are disclosed in U.S. Pat. No. 5,707,967 as effective against headache; certain water soluble amino carboxylic acid compounds are disclosed in U.S. Pat. No. 5,708,029 as effective against elevated blood pressure, and certain water soluble amino carboxylic acid compounds are disclosed in U.S. Pat. No. 5,767,157 as effective against pain in a joint.

SUMMARY OF THE INVENTION

In accordance with this invention, there is provided a method of treating ill effects of alcohol ingestion in a person in need of such treatment, which comprises the administration to such person of at least one aliphatic sulfur compound. Administration of the aliphatic sulfur compound according to the invention is believed to enhance the effectiveness of the human immune system and thereby mitigate the hangover condition.

The aliphatic sulfur compound preferably includes a sulfur-methylene moiety such as

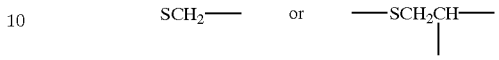

More preferably, the aliphatic sulfur compound also includes a carboxyl group, as in

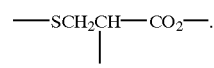

Still more preferably, the aliphatic sulfur compound is a sulfur-containing amino-acid derivative of an ethyl sulfide having the formula (I)

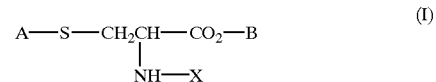

in which A is hydrogen or a carboxymethylene —CH$_2$CO$_2$H group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

In this compound, the ethyl sulfide group

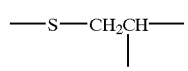

is believed to be responsible for the beneficial activity observed while the attached groups A, —NHX, and —CO$_2$B assist in delivering the compound to the site within the human organism where the beneficial activity is exerted.

In one preferred embodiment, A is hydrogen.

In a further preferred embodiment, A, B, and X are not simultaneously hydrogen.

Particularly suitable illustrative derivatives having the formula given above are tabulated by showing the assignments of A, B, and X in the above formula:

| Compound | A | B | X |
|---|---|---|---|
| 1 | —CH$_2$CO$_2$H | H | H |
| 2 | H | H | COCH$_3$ |
| 3 | H | CH$_3$ | H.HCl |
| 4 | H | C$_2$H$_5$ | H.HCl |
| 5 | H | H | H |
| 6 | H | H | H.HCl |

The present invention is based on the recognition that enhancing the effectiveness of the immune system in a person can be beneficial in augmenting the person's innate ability to resist the initiation and intensification of the uncomfortable and potentially dangerous after-effects of consumption of alcohol, particularly consumption in excess of the body's normal tolerance. Consequently, the quality of life is improved.

In increasing the effectiveness of the human immune system according to this invention, mega-nutrient doses of 2 to 20 grams of a compound or compounds of formula (I) can be administered to a victim after signs of hangover appear and up to five times a day in order to diminish its extent and duration. Such doses can also be administered in advance of or simultaneously with consumption of alcohol. Doses can be administered in any convenient manner, as by oral administration in any of the usual dosage forms, such as tablets, capsules, solutions, and dispersions in liquid foods such as soups and fruit juices. Alternatively, there can be given sterile solutions by direct injection into the bloodstream of the person to be treated, as well as by rectal suppositories.

EXAMPLE 1

Numerous individuals (twelve men and three women) have taken 10 gram doses hourly on an empty stomach after a hangover and experienced relief within one hour and disappearance of the symptoms within three hours.

EXAMPLE 2

Volunteers were tested to determine a threshold quantity of alcohol (i.e. ounces of vodka given with a slice of bread on an empty stomach) giving rise to symptoms of impairment such as inability to walk 25 feet in a straight line within 30 minutes. One group of volunteers served as a control group. A second group received 20 grams of composition containing several compounds of formula (I) at the same time as the alcohol. A third group received 40 grams of the same composition at the same time.

The average threshold quantity of alcohol for the members of the group receiving 40 grams of composition containing compounds of formula (I) was more than twice the average threshold quantity for the members of the control group.

What is claimed is:

1. A method of treating after-effects of alcohol consumption in a person in need of such treatment, which comprises the administration to such person of mega-nutrient doses of 2 to 20 grams up to five times daily of at least one sulfur-containing amino-acid derivative having that formula (I)

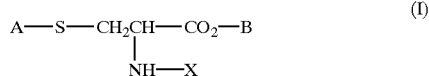

in which A is hydrogen or carboxymethylene —CH$_2$CO$_2$H group, B is hydrogen or an alkyl group having 1 to 3 carbon atoms, and X is hydrogen or an acyl group —CO—R in which R is an alkyl group having 1 to 3 carbon atoms, or a pharmaceutically acceptable salt of such compound, provided that the total dose is al least 10 grams daily and not in excess of 100 grams daily.

2. The method of claim 1, wherein said amino-acid derivative is administered orally when said after-effects are observed.

3. The method of claim 1 wherein said amino-acid derivative is administered orally prior to or simultaneously with consumption of alcohol.

4. The method of claim 1, wherein said amino-acid derivative is administered by injection into the bloodstream.

5. The method of claim 1, wherein said amino-acid derivative is administered by rectal suppository.

6. The method of claim 1, wherein the total of said amino-acid derivative administered daily is in the range of 10 to 80 grams.

7. The method of claim 1, wherein said amino-acid derivative is the compound of formula (I) in which A is —CH$_2$CO$_2$H, B is H, and X is H.

8. The method of claim 1, wherein said amino-acid derivative is the compound of formula (I) in which A is H, B is H, and X is COCH$_3$.

9. The method of claim 1, wherein said amino-acid derivative is the compound of formula (I) in which A is H, B is CH$_3$, and X is H.HCl.

10. The method of claim 1, wherein said amino-acid derivative is the compound of formula (I) in which A is H, B is C$_2$H$_5$. and X is H.HCl.

11. The method of claim 1, wherein said amino-acid derivative is the compound of formula (I) in which A is H, B is H, and X is H.

12. The method of claim 1 wherein said amino-acid derivative is the compound of formula (I) in which A is H, B is H, and X is H.HCl.

13. The method of claim 1, wherein said person experiences an increased threshold quantity of alcohol to produce said after-effects.

14. The method of claim 1 wherein after treatment said after-effects are not observed.

15. The method of claim 1, wherein a plurality is the compound of formula (I) is administered.

16. The method of claim 1, wherein said amino-acid derivative is administered in one to five daily doses of 20 grams each.

17. The method of claim 1, wherein said amino-acid derivative administered in five daily doses of 2 to 20 grams each.

18. The method of claim 1 wherein the total of said amino-acid derivative administered daily is 20 grams.

19. The method of claim 1, wherein the total of said amino-acid derivative administered daily is 100 grams.

20. A method of treating after-effects of alcohol consumption in a person in need of such treatment, which comprises enhancing the effectiveness of the person's immune system by the administration to such person of mega-nutrient doses of 2 to 20 grams up to five times daily of at least one sulfur-containing amino-acid derivative having the formula (I)

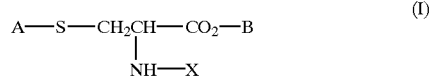

in which A is hydrogen or carboxymethylene —CH$_2$CO$_2$H group, B is hydrogen or an alkyl group having 1 to 3 carbon atoms, and X is hydrogen or an acyl group —CO—R in which R is an alkyl group having 1 to 3 carbon atoms, or a pharmaceutically acceptable salt of such compound, provided that the total dose is at least 10 grams daily and not in excess of 100 grams daily.

21. The method of claim 20, wherein the total of said amino-acid derivative administered daily is in the range of 10 to 80 grams.

22. The method of claim 20, wherein said amino-acid derivative is the compound of formula (I) in which A is H, B is H, and X is COCH$_3$.

23. The method of claim 20, wherein a plurality of compounds of formula (I) is administered.

* * * * *